US012001781B2

(12) United States Patent
Bini

(10) Patent No.: US 12,001,781 B2
(45) Date of Patent: Jun. 4, 2024

(54) QUERY SELECTION SYSTEM

(71) Applicant: Evernorth Strategic Development, Inc., St. Louis, MO (US)

(72) Inventor: Mark G. Bini, O'Fallon, MO (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 309 days.

(21) Appl. No.: 17/482,306

(22) Filed: Sep. 22, 2021

(65) Prior Publication Data

US 2022/0092255 A1   Mar. 24, 2022

Related U.S. Application Data

(60) Provisional application No. 63/082,321, filed on Sep. 23, 2020.

(51) Int. Cl.
| | | |
|---|---|---|
| *G06F 17/00* | (2019.01) | |
| *G06F 16/2457* | (2019.01) | |
| *G06F 40/174* | (2020.01) | |
| *G16H 10/20* | (2018.01) | |
| *G16H 50/80* | (2018.01) | |

(52) U.S. Cl.
CPC ...... *G06F 40/174* (2020.01); *G06F 16/24575* (2019.01); *G16H 10/20* (2018.01); *G16H 50/80* (2018.01)

(58) Field of Classification Search
CPC . G06F 40/174; G06F 16/24575; G16H 10/20; G16H 50/80; G16H 20/10; G16H 40/67
See application file for complete search history.

(56) References Cited

U.S. PATENT DOCUMENTS

| | | |
|---|---|---|
| 6,999,987 B1 | 2/2006 | Billingsley |
| 7,103,556 B2 | 9/2006 | Del Rey |
| 7,519,577 B2 | 4/2009 | Brundage |
| 8,955,058 B2 | 2/2015 | Castro |
| 9,195,822 B2 | 11/2015 | Carlson |
| 9,305,059 B1 | 4/2016 | Glickman |

(Continued)

OTHER PUBLICATIONS

Qualtrics, Question Randomization, https://www.qualtrics.com/support/survey-platform/survey-module/block-options/question-randomization/, accessed Aug. 11, 2020.

*Primary Examiner* — Greta L Robinson
(74) *Attorney, Agent, or Firm* — Schwegman Lundberg & Woessner, P.A.

(57) ABSTRACT

Methods and systems for a query selection system are provided. The methods and systems include operations comprising: accessing a database comprising a plurality of data inquiries, a data inquiry of the plurality of data inquiries being associated with inquiry metadata including a data type, a data inquiry, a plurality of data responses, and display data; accessing a query definition group, the query definition group defining a plurality of data types to include in a data inquiry prompt; accessing historical query selection information representing one or more data inquiries of the plurality of data inquiries previously presented to one or more users; configuring, based on the query definition group and the historical query selection information, a set of the plurality of data inquiries; and generating the data inquiry prompt based on the configured set of the plurality of data inquiries.

21 Claims, 12 Drawing Sheets

(56) References Cited

U.S. PATENT DOCUMENTS

| | | |
|---|---|---|
| 9,497,178 B2 | 11/2016 | Chow |
| 9,516,008 B2 | 12/2016 | Chow |
| 9,836,778 B2 | 12/2017 | Lyman |
| 10,445,508 B2 * | 10/2019 | Sher-Jan ............. H04L 63/1433 |
| 10,565,509 B2 | 2/2020 | London |
| 10,621,880 B2 | 4/2020 | Boguraev |
| 10,692,159 B2 | 6/2020 | Charkov |
| 10,726,079 B2 | 7/2020 | Makaremi |
| 10,733,546 B2 | 8/2020 | Pilkington |
| 10,834,221 B2 | 11/2020 | Tong |
| 2004/0267704 A1 | 12/2004 | Subramanian |
| 2006/0154642 A1 * | 7/2006 | Scannell ................ G08B 7/066 |
| | | 455/404.1 |
| 2007/0239516 A1 | 10/2007 | Smith |
| 2013/0103434 A1 | 4/2013 | Cazeaux |
| 2015/0339393 A1 | 11/2015 | Chung |
| 2017/0032394 A1 | 2/2017 | Stevens |
| 2018/0054710 A1 * | 2/2018 | Gum ...................... G16H 50/30 |
| 2019/0052720 A1 | 2/2019 | Guo |
| 2019/0138734 A1 * | 5/2019 | Sher-Jan ............... G06F 21/577 |
| 2019/0272925 A1 * | 9/2019 | Barrett ................... G16H 50/80 |
| 2020/0042577 A1 | 2/2020 | Kasa |
| 2020/0241895 A1 * | 7/2020 | Voss ..................... G06F 40/205 |
| 2020/0322703 A1 | 10/2020 | Bures |

* cited by examiner

─ 300

DATA INQUIRY METADATA

─ 310
<Data Type>
    <Health Related>
    <Region> Any <Region>
    <Industry> Any </Industry>
    <Infection Rate> Any </Infection Rate>
</Data Type>

─ 320
<Data Inquiry>
    <"Have you or your family experienced health related symptoms like fatigue or fever in the past 24 hours">
</Data Inquiry>

─ 330
<Data Responses>
    <"Yes">
    <"No">
</Data Responses>

<Display Data> ─ 340
    <Spelling Error>
    <Grammatical Error>
    <Font> type, size, color
    <Position Randomization>
    <Presentation Format>
        <Individual>
        <Background Fill>
    </Presentation Format>
</Display Data>

HISTORICAL QUERY SELECTION INFORMATION

*410
<Inquiry ID>
    <UNIQUE IDENTIFIER OF QUERY METADATA>
</Inquiry ID>

*420
<Data Inquiry Information>
  <Group ID> XYX
    <USER ID 1> *422
      <Display Date> March 14
      <Display Data>
        <Font 1, No Grammar Errors, No Background fill, position 3>
      </Display Data>
    <USER ID 2> *424
      <Display Date> March 14
      <Display Data>
        <Font 2, Grammar Errors Present, No Background fill, position 2>
      </Display Data>
    <USER ID 3> *426
      <Display Date> March 17
      <Display Data>
        <Font 2, Grammar Errors Present, No Background fill, position 2>
      </Display Data>
  </Group ID>

</Data Inquiry Information>
- •
- •
- •

*FIG. 4*

Welcome Jon!!

Set Up Your Profile Below:

Where do you live? — 510 [Florida]

Select Industry — 520 [School]

Which class is your child in? — 530 [Guppies]

Welcome Jon!

March 14 — 620

Please respond truthfully below:

610 — Have you or your family experienced health related symptoms like fatigue or fever in the past 24 hours? [Yes] [No]

Have you had contact with someone who tested positive for the infection? [Yes] [No]

Have you left the country in the past 72 hours? [Yes] [No]

630 — Have you been tested for infection in the past week? [Yes] [No]

Welcome Jon!!

720 — March 17

Please respond truthfully below:

Have you had contact with someone who tested positive for the infection?
- Yes
- No Have you left the country in the past 72 hours?
- Yes
- No Have you been tested for infection in the past week?
- Yes
- No

710

Have you or your family experienced health related symptoms like fatigue or fever in the past 24 hours?
- Yes
- No

Welcome Charlie!!

March 17 — 820

Please respond truthfully below:

Have you had contact with someone who tested positive for the infection?
- Yes
- No Have you left the country in the past 72 hours?
- Yes
- No Have you been tested for infection in the past week?
- Yes
- No Haven't you experiencing health rlatd symptoms like fatigue or fevler in the plest 24 hours? — 810
- Yes
- No

FIG. 8

QUERY SELECTION SYSTEM

CROSS-REFERENCE TO RELATED APPLICATION

This application claims priority to and is a non-provisional of U.S. Provisional Application No. 63/082,321, filed Sep. 23, 2020, which is hereby incorporated by reference in its entirety.

BACKGROUND

Users are increasingly using websites via the Internet to access information and perform transactions. For example, users can access websites to complete surveys, including questionnaires relating to health information that are used to control social spread of infection among individuals within a community.

BRIEF DESCRIPTION OF THE DRAWINGS

FIGS. 3 and 4 are block diagrams of example data structures that may be deployed within the database of FIG. 2, according to some embodiments.

FIGS. 5-8 are illustrative graphical user interfaces of the query selection system, according to some embodiments.

DETAILED DESCRIPTION

Figure 1:
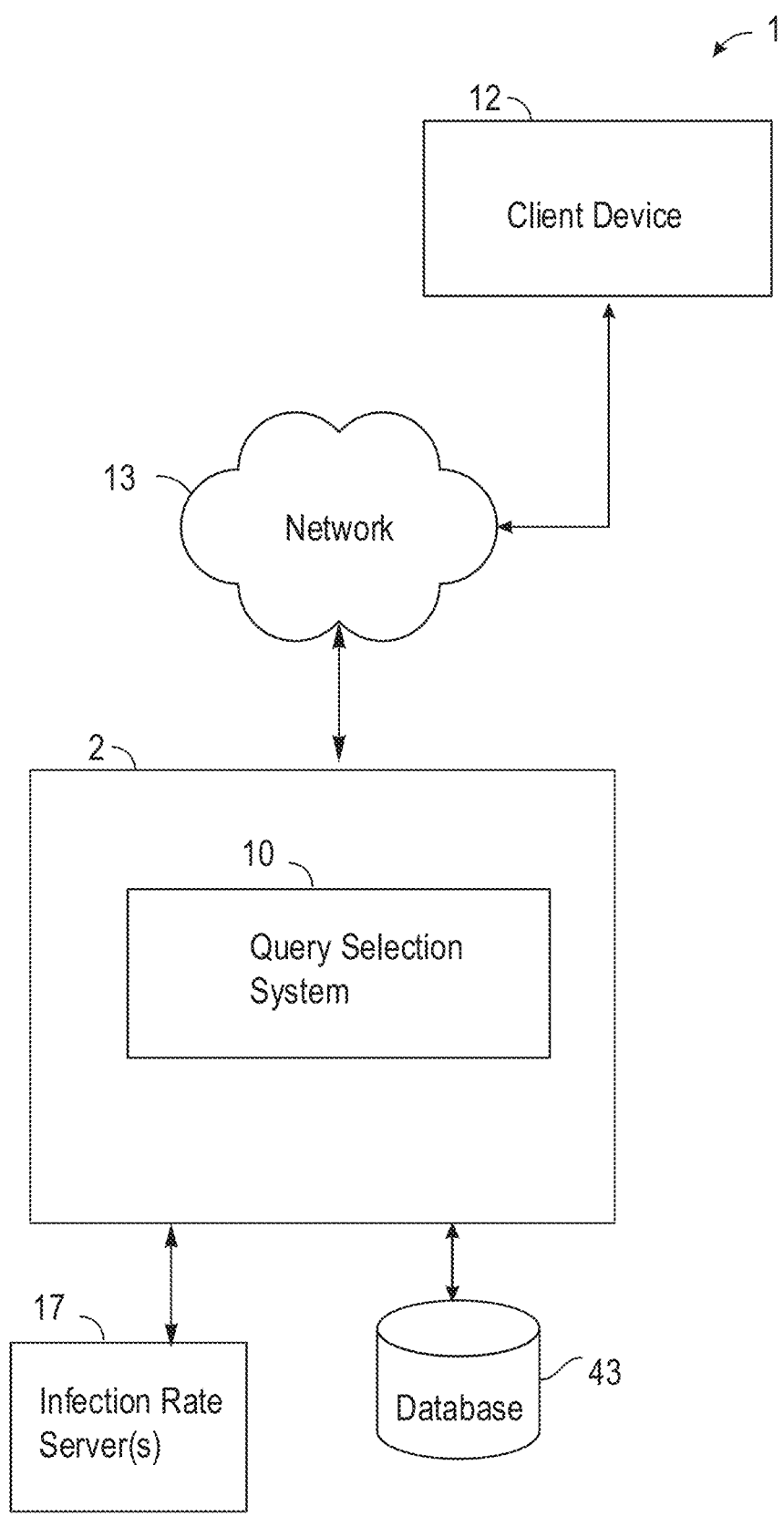
FIG. 1 is a block diagram of an example query selection system, according to some embodiments.

Example methods and systems for a query selection system are described. In the following description, for purposes of explanation, numerous specific details are set forth in order to provide a thorough understanding of example embodiments. It will be evident, however, to one of ordinary skill in the art that embodiments of the invention may be practiced without these specific details.

As the world begins to return to worksites and children are being sent back to school, digital applications that require people (employees, students, parents, etc.) to complete daily attestations of their personal health (symptoms, temperature, etc.), social behaviors (social distancing precautions, contact with people who are positive with an infectious disease, e.g., the novel coronavirus (COVID-19 or COVID), etc.) and whereabouts (travel outside of the country, etc.) are becoming more common. For example, such attestations can be submitted as responses to questionnaires or surveys, which can be supported by computing systems and/or electronic devices.

Users can access an online questionnaire to answer various social and health related questions. The online questionnaire can be displayed by an electronic device with a human-to-machine interface and provided to the electronic device from an electronic server. These questionnaires are used to control social spread of infection among individuals. As such, maintaining accuracy and truthfulness in the responses to the questionnaires is of utmost importance. Typical systems present the questions in these questionnaires in a generic format, which is provided in the same format to everyone, and to the same person in successive presentations. Users who repeatedly are presented these electronic questionnaires on a daily or weekly basis become accustomed to the lineup or the order of the questions and their corresponding responses. After responding to the same questions a certain number of times, users may start to use muscle memory to blindly or automatically answer the questions through an electronic device without carefully considering the questions. The users may interact with the online questionnaire on an electronic device in a mechanical or habitual repetitive manner. The users may not be mindful in their interaction with the questions displayed. For example, if the first question that is asked on the questionnaires is always the same, the users may start to automatically respond to the question based on their previous response to the question even though their current situation may have changed. This rote behavior calls into question the veracity of the responses to the questionnaires and the overall reliability of the questionnaires.

The disclosed embodiments provide systems and methods to generate query selections for an inquiry prompt in a manner that enhances the likelihood of a user reading each individual inquiry in the inquiry prompt. Specifically, the disclosed embodiments vary the presentation format as well as the ordering, timing, positioning, or combination thereof of the questions in the inquiry prompt. In this way, users who frequently and repeatedly answer the same inquiries cannot rely on their muscle memory or mental habit to answer the questions. Namely, because the inquiries are presented in different ways, such as using different presentation formats, and in different orders, e.g., on an electronic device, the users have to pay close attention to the questions being asked and the answers they provide. These changes in the questions or display of the form may increase the mindfulness of the user. In particular, the disclosed embodiments access a database comprising a plurality of data inquiries, a data inquiry of the plurality of data inquiries being associated with inquiry metadata including a data type, a data inquiry, a plurality of data responses, and display data. The disclosed embodiments access a query definition group, the query definition group defining a plurality of data types to include in a data inquiry prompt and historical query selection information representing one or more data inquiries of the plurality of data inquiries previously presented to one or more users. The disclosed embodiments configure, based on the query definition group and the historical query selection information, a set of the plurality of data inquiries and generate the data inquiry prompt based on the configured set of the plurality of data inquiries.

In this way, the veracity of responses to questionnaires and the overall reliability of the questionnaires is enhanced by the disclosed embodiments. This improves the ability for employers, communities and schools to control the social spread of infection among individuals.

FIG. 1 is a block diagram showing an example system 1 according to various exemplary embodiments. The system 1 can be a query selection system, such as a mobile electronic questionnaire or survey system, that includes a query selection server system 2, an infection rate server 17, a database 43, and a client device 12 that are communicatively coupled over a network 13 (e.g., Internet, telephony network).

While FIG. 1 illustrates a single client device 12, it is understood that a plurality of client devices 12 can be included in the system 1 in other embodiments. As used herein, the term "client device" may refer to any machine that interfaces to a communications network (such as network 13) to obtain resources from one or more server systems or other client devices and provide a user with the ability to response to inquiries provided by the query selection system 10. The client device includes an inquiry application that is locally installed on the client device and/or a web browser application that accesses the query selection system 10 over the Internet and responds to an online questionnaire provided by the query selection system 10. In case the inquiry application is locally installed, the local application is in communication with the query selection system 10 to obtain one or more inquiries configured to be generated in a data inquiry prompt. A data inquiry prompt may be a visual interface element that includes a plurality of questions and corresponding multiple choice answers all displayed together. In another embodiment, the data inquiry prompt may present different groups of questions and corresponding multiple choice responses sequentially on separate pages and/or across different types of client or input devices. The data inquiry prompts can each be an individual graphical user interface.

A client device may be, but is not limited to, a mobile phone, desktop computer, laptop, portable digital assistant (PDA), smart phone, a wearable device (e.g., a smart watch), tablet, ultrabook, netbook, laptop, multi-processor system, microprocessor-based or programmable consumer electronic, game console, set-top box, or any other communication device that a user may use to access a network. These devices upon receiving instructions to perform tasks according to the teachings of the present disclosure become dedicated machines as their processing circuitry is dedicated for these tasks by loading the machine instructions from memory. These devices further have displays for presenting the queries, e.g., in a unique manner, upon successive logins by a same person or for no two people to receive the same question presentation on the display.

The network 13 may include, or operate in conjunction with, an ad hoc network, an intranet, an extranet, a virtual private network (VPN), a local area network (LAN), a wireless network, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

In the example shown in FIG. 1, a user using the client device 12 can establish a communication session with the query selection system 10, such as via a website. In one example, the client device 12 scans a barcode or QR code that is presented on a board or another device. Scanning the barcode or QR code causes the client device 12 to access a website associated with the query selection system 10 to present the user with a set of inquiries.

The client device 12 may log into the query selection system 10 to access a previously generated profile for the user of the client device 12. If this is the first time the user is logging into the query selection system 10, the query selection system 10 presents a user interface (e.g., on an electronic device) that allows the user to set up a profile. The profile allows the user to specify the purpose of the communication session, such as dropping kids off at schools, going to work, boarding a plane, accessing a community resource, such as a gym or a pool, or other public gathering. The profile also allows the user to specify the user's current geographical location. The profile allows the user to create a username and password that will be used in the future to access the profile for the user.

After the user logs into the query selection system 10, the query selection system 10 identifies a group associated with the user based on the profile set up for the user. For example, the query selection system 10 retrieves a set of inquiries associated with dropping kids of at school if the profile was set up for this purpose. In addition, the query selection system 10 retrieves a set of inquiries associated with the geographical location of the user. In some cases, the query selection system 10 retrieves one or more additional inquiries based on an infection rate of a given disease in a particular region. If the infection rate is above a threshold, a first set of inquiries can be retrieved and if the infection rate is below the threshold, a second set of inquiries can be retrieved. The first set of inquiries may include a particular question and the second set of inquiries may exclude the particular question. In some cases, the first set of inquires may include a repeated question and the second set of inquires only include one instance of the particular question.

In one example, a particular region associated with a profile may be associated with a low rate of infection (e.g., the query selection system 10 accesses one or more infection rate server(s) 17 to determine that the infection rate associated with the region is below a threshold). In this case, the query selection system 10 selects the second set of inquiries or a set of inquiries associated with a low rate of infection. The user may be presented with an inquiry prompt that includes the second set of inquiries. At a later time, such as one week later, the same user may access the query selection system 10 again to answer the set of questions. The query selection system 10 obtains the current rate of infection associated with the particular region (e.g., the rate of infection that is one week after the last time the user accessed the set of inquiries) from one or more infection rate server(s) 17. The query selection system 10 determines that now the rate of infection is greater than the threshold and, in response, selects the first set of inquiries to present to the user in the inquiry prompt. In this way, the type of questions provided to the user in the inquiry prompt vary based on the current rate of infection in the region associated with the user.

In one embodiment, to access the current infection rate for a particular region, the query selection system 10 obtains the geographical region from a profile associated with the user. The query selection system 10 provides that region to the infection rate server 17. The infection rate server 17 may be a publicly available database of infection rates that is operated or updated by the Center for Disease Control (CDC) or other medical tracking organization. The infection rates stored in the infection rate server 17 may represent the number of positive infections over a given time interval relative to the number of negative infections or relative to the number of tests that are administered. The infection rate may alternatively, or in addition, may be a function or factor of the number of hospitalizations relative to the number or percentage of positive infections in the region.

In another example embodiment, the infection rate server 17 can process medication adherence or vaccination data from a pharmacy or a pharmacy benefits to trigger a query process. When a drug is discovered to have an adherence or vaccination issue, e.g., when patients are not adherent as determined by the pharmacy or when non-adherence is above a threshold, the pharmacy server can trigger a query process to a patient, group of patients or care providers.

The query selection system 10 accesses, from the database 43, a list of previously presented inquiries associated with the profile. For example, after presenting a list of inquiries to the user at one point in time, the query selection system 10 stores, e.g., in the database 43, an indication in the profile of various attributes of the inquiries. Specifically, the query selection system 10 stores the presentation order of the questions (e.g., which question was presented first and which questions followed the first question) in the database 43. The query selection system 10 also stores in the profile the display or presentation format of one or more of the questions which were presented to the user. For example, the query selection system 10 stores an indication in the database 43 of whether a certain graphical property, such as a background was used for the one or more questions, whether spelling or grammatical errors were purposefully introduced in the one or more questions, the font style, size and color used to present the one or more questions, and so forth. This information pertaining to the presentation order and format or style of the previously presented questions is stored in association with the user's profile as historical query selection information in the database 43. The query selection system 10 can also introduce timing changes into the questions being selected, e.g., by altering the time between presentation of the questions.

The query selection system 10 configures the set of inquiries that are retrieved based on the profile of the user. Specifically, the query selection system 10 configures the set of inquiries based on the historical query selection information stored for the user and/or based on a vaccination status of the user. The query selection system 10 configures the set of inquiries to avoid repeating the same presentation order and/or format for the questions presented to the same user. In some cases, the query selection system 10 avoids repeating the same presentation order and/or format for the questions presented to the user over a given time interval (e.g., within the same week, month, year, decade, and so forth). In this way, different questions or inquiries (e.g., the same set of inquiries but with different presentation formats or orders) are presented to a parent who repeatedly accesses a questionnaire when dropping their child of at a school. As another example, different questions or inquiries (e.g., the same set of inquiries but with different presentation formats or orders) are presented to an employee who repeatedly accesses a questionnaire when arriving at an employer's building. As another example, different questions or inquiries (e.g., the same set of inquiries but with different presentation formats or orders) are presented to a user who repeatedly accesses a questionnaire when arriving at facility, such as a gym or pool, in a community. As another example, different questions or inquiries (e.g., the same set of inquiries but with different presentation formats or orders) are presented to a user who has been vaccinated against a target infection versus another user who has not been vaccinated against the target infection.

In some cases, the query selection system 10 configures the set of inquiries based on profile information (historical query selection information) stored in profiles of other users that are in the same group as the user. For example, if the user is a parent in a given child's class, that class is associated with a group identifier. The query selection system 10 configures the set of inquiries based on other parents associated with the same group identifier (e.g., other parents of children in the same class or school). The query selection system 10 configures the set of inquiries to avoid repeating the same presentation order and/or format for the questions presented to each user in a particular group of users, such as within a given time interval. In this way, different questions or inquiries (e.g., the same set of inquiries but with different presentation formats or orders) are presented to parents of children who are in the same class in a school. As another example, different questions or inquiries (e.g., the same set of inquiries but with different presentation formats or orders) are presented to each employee in an organization who repeatedly accesses a questionnaire when arriving at an employer's building. As another example, different questions or inquiries (e.g., the same set of inquiries but with different presentation formats or orders) are presented to users who live in the same community who repeatedly accesses a questionnaire when arriving at facility, such as a gym or pool, in the community.

In one example, the query selection system 10 randomizes the order of various questions that are presented to a user on a client device 12. The query selection system 10 also randomizes which questions of the set of questions will have a presentation format modified. In some cases, a particular question in a set of questions presented to the user is associated with an indicator that specifies the particular question is to be presented with a presentation format that differs from that of the other questions in the set. In such circumstances, the query selection system 10 randomly selects a presentation format for the particular question, such as to introduce a spelling error, a grammatical error, a punctuation error, use certain font style, color, and size, apply a background to the question, and any combination thereof. The query selection system 10 then presents the particular question in an inquiry prompt with the randomly selected presentation format and in the randomly selected order.

The query selection system 10 presents an inquiry prompt that includes the set of inquiries to the client device 12. The user of the client device 12 views the questions and selects a response from a set of responses associated with each question. The query selection system 10 stores the response in the profile associated with the user together with the presentation order and/or format used to present each question in the inquiry prompt.

In an example embodiment, the query selection system 10 can also insert a random question into the questions being presented on the display. A random question can be a red herring type of question. The questions of interest include questions relating to healthtracking, in contrast, the random question can be about the weather, an A/B test question that does not relate to the health information questions. For example, query selection system 10 can randomly select the random question and randomly select wherein the order of actual tracking questions this question is presented. Examples of random questions include "how is the weather today?", "is it raining?", "is your favorite color blue?", "do you like _____?" and similar queries that are not germane to the attestation. Some of these extraneous questions are directed toward the user's experience or personal preferences and cause the user to be mindful about the answer. The system need not store the responses to the questions that are not germane.

Figure 2:
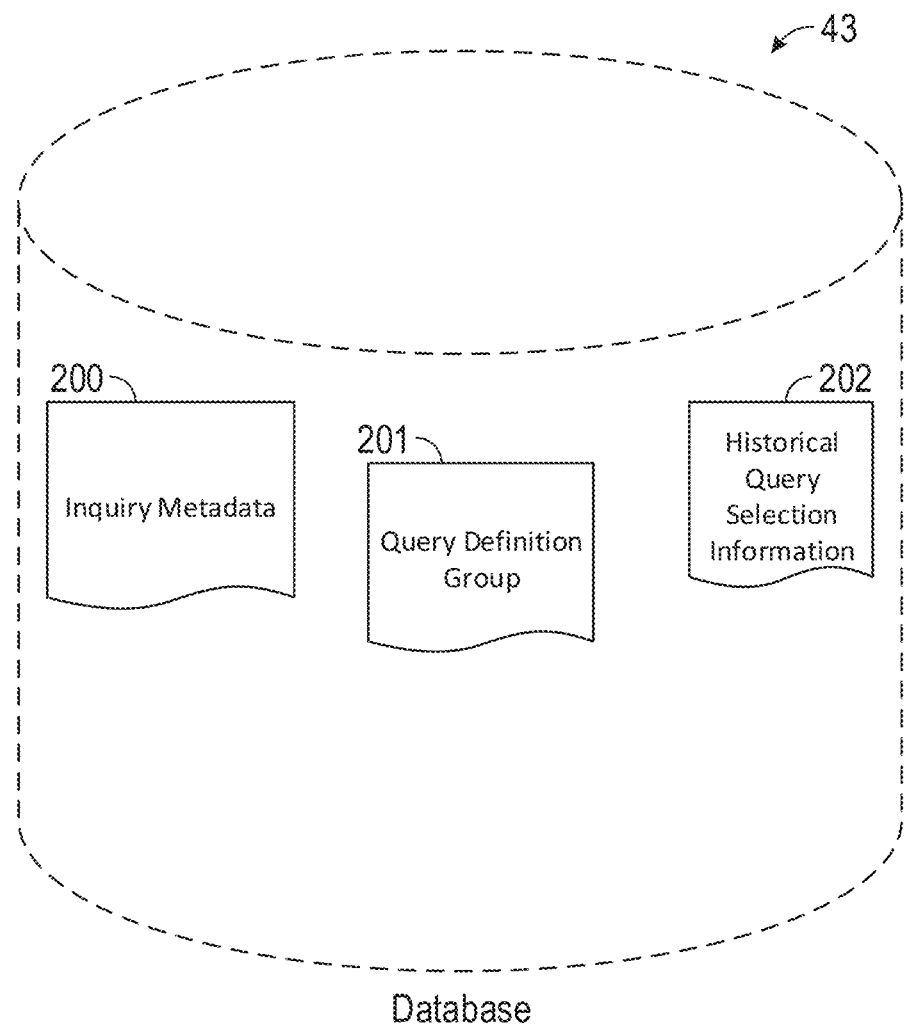
FIG. 2 is block diagram illustrating further details regarding a database used by the query selection system, according to some embodiments.

FIG. 2 is block diagram illustrating further details regarding a database 43 used by the query selection system 10, according to some embodiments. The database 43 includes inquiry metadata 200, query definition group 201, and historical query selection information 202. The inquiry metadata 200 stores a plurality of data inquiries. Each data inquiry of the plurality of data inquiries is associated with inquiry metadata including a data type, a data inquiry, a plurality of data responses, and display data. The display data of one or more of the inquiries defines various presentation formats or graphical properties for one or more of the inquiries, such as different font styles, colors, and sizes, different background colors used to present the particular inquiry, difference grammatical, spelling or punctuation errors introduced in the inquiry, timing and so forth. In some implementations, a first data inquiry of the plurality of data inquiries is associated with a first data type that includes at least one of health related information, vaccination status, social related information, geographical information, infection rate information, and/or industry related information. In some implementations, a second data inquiry of the plurality of data inquiries is associated with a second data type, different form the first data type, that includes at least one of the health related information, the social related information, the geographical information, the infection rate information, and/or the industry related information. The health related information represents symptoms of a disease or virus, vaccination status and the social related information represents travel information, location information, and social interaction information, and the industry related information includes schools, retail, and manufacturing.

The query definition group 201 stores a list of inquiry identifiers associated with a particular group. For example, a school group may be associated with a first set of query identifiers that identifies the quantity of health related questions, social related questions and industry related questions for the school group. The school group may store specific inquiry identifiers to ensure that those questions are included in an inquiry prompt and/or may cause the specified quantity of questions associated with the particular question types to be randomly selected and randomly positioned. As another example, an employment group may be associated with a second set of query identifiers that identifies the quantity of health related questions, social related questions and industry related questions for the employment group. As another example, vaccination group may be associated with a third set of query identifiers that identifies the quantity of health related questions, social related questions and industry related questions for the vaccination group (the vaccination group can represent vaccinated or unvaccinated individuals). The quantity and type of questions provided to one group may be the same or different from the quantity and type provided to another group.

FIG. 3 shows a block diagram of an example data structure 300 that may be deployed within the database of FIG. 2, according to some embodiments. Specifically, data structure 300 is an example of the inquiry metadata 200 for a plurality of inquiries. The data structure 300 includes a plurality of fields including a data type field 310, a data inquiry field 320, a data responses field 330 and a display data field 340. The data type field 310 associates a particular inquiry with an indication of whether the inquiry is a health related question, a social related question or industry related question. In this way, the question selection system 10 can use the data type field 310 to ensure that a predetermined or specified number of inquiries are retrieved that are associated with a first type of data (e.g., are health related questions) and another predetermined or specified number of inquiries are retrieved that are associated with a second type of data (e.g., are social related questions). The data type field 310 also stores an association of a region for each inquiry to enable the question selection system 10 to narrow down selection of the questions by region (e.g., a particular city or state may be presented with one set of questions and another city or state may be presented with a different set of questions).

The data type field 310 also stores an association of an industry for each inquiry to enable the question selection system 10 to narrow down selection of the questions by industry (e.g., a mode of transportation, such as plane or bus, may be presented with one set of questions and another mode of transportation may be presented with a different set of questions; or questions presented for users associated with a school are presented with different questions than questions presented to users going to work at an organization or building). The data type field 310 also stores an association of an infection rate (or vaccination state) for certain inquiries to enable the question selection system 10 to include or exclude certain questions based on whether the infection rate exceeds a threshold or not (and/or based on the vaccination state of an individual as specified by the profile). The infection rate stored in the data type field 310 may be the threshold against which the current infection rate is compared. In this way, different inquiries may be associated with different infection rate thresholds to control whether or not they are included in an inquiry prompt.

The data inquiry field 320 includes the text or graphic content represent the question or prompt. The data responses field 330 includes the multiple choice responses associated with the question or prompt specified in the data inquiry field 320. The display data field 340 stores a list of different presentation formats for presenting the content of the data inquiry field 320 and data responses field 330.

FIG. 4 shows a block diagram of an example data structure 400 that may be deployed within the database of FIG. 2, according to some embodiments. Specifically, data structure 400 is an example of the historical query selection information 202. The data structure 400 includes an inquiry ID field 410 and a data inquiry information field 420. The inquiry ID field 410 stores an identifier of the data inquiry metadata data structure 300 of each question previously presented to a given user. The data structure 400 may be associated with a particular user or a group of users associated with a same or common group identifier. As each question is presented to a user and/or as each question is answered by a given user, the identifier associated with the question is retrieved and stored in the data structure 400 associated with the user and/or group associated with the user.

The data inquiry information field 420 stores group identifier information for a given user and the display data and time of the question associated with the inquiry identifier field 410. Namely, when the question is presented to a particular user, the query selection system 10 obtains the display format of the question from the display data field 340 associated with the question. The query selection system 10 stores the display format of the question that is retrieved from the display data field 340 in the data inquiry information field 420. For example, if the question was presented with a blue background and with two spelling mistakes that were intentionally introduced, this information about the display format is stored in the data inquiry information field 420. In some cases, the display format is stored in association with a given identifier of the user to whom the question was presented.

For example, the data inquiry information field 420 may list a plurality of users who are associated with the same group ID and may store for each of the users the display format of the same question associated with the inquiry identifier field 410 as the question was presented to the user. Specifically, if a first question was presented to a first user associated with a first user identifier 422 with a first display format that includes a spelling mistake and a grey background, the data inquiry information field 420 stores this first display format in association with the first user identifier 422 for the inquiry identifier 410 associated with the first question. If the first question was presented to a second user (who is in the same group as the first user) associated with a second user identifier 434 with a second display format that includes a punctuation error that is intentionally introduced and a green background, the data inquiry information field 420 stores this second display format in association with the second user identifier 424 for the inquiry identifier 410 associated with the first question. The query selection system 10 also stores the timestamp representing when the particular questions were presented to each of the users in the group.

Based on the information contained in the data structure 400, the query selection system 10 can ensure that a different display format is used to present the same question to the same user on different time intervals and/or to different users in a group of users in the same time interval or different time intervals. For example, the query selection system 10 may select to include in a set of inquiries the first question to present to a third user associated with a third user identifier 426. The query selection system 10 may determine that the first question was presented within the past three days with first, second, and third display formats based on the information included in the data inquiry information field 420 to the same user and/or to other users in the same group as the third user. In this case, the query selection system 10 may select from the data inquiry metadata structure 300 associated with the first question an alternate display format from the display data field 340 that is different from the first, second and third display formats. In some cases, the alternate display format may be selected at random from a set of available display formats stored in the display data field 340.

FIGS. 5-8 are illustrative graphical user interfaces of the query selection system, according to example embodiments. For example, user interface 500 (FIG. 5) may be presented to a user the first time they access the query selection system 10. The user interface 500 allows the user to set up their profile, such as to cause a relevant set of questions to be presented to the user whenever the user drops off their child at school. The profile generates the group identifier for the user and associates the user with the group identifier. As an example, the user interface 500 includes a first question asking the user to specify where they live to establish the geographical region associated with the user. The user interface 500 includes a second question asking the user to specify the purpose of the profile, specify whether the user is vaccinated against the target infection, and select the industry for the user to establish the industry associated with the user. The user interface 500 may also allow the user to select a particular group 530 with which to associate the user, such as a particular classroom within a school.

The user interface 600 may be presented to a user that includes a data inquiry prompt. The user interface 600 may be presented when the user scans a barcode or QR code or when the user accesses a locally installed application. This user interface 600 may be presented, for example, when a parent drops off their child at school after logging in and identifying themselves to the query selection system 10. The user interface 600 includes the current date 620 and a list of questions 610. The list of questions 610 correspond to questions obtained by the query selection system 10 based on the group identifier or user profile information associated with the user. The list of questions 610 correspond to the region or industry associated with the user. In some cases, the query selection system 10 presents a particular question 630 that is associated with a certain display format. The particular question 630 may be randomly positioned at a different position relative to the other questions on the user interface 600 each time the user accesses the user interface 600 on different days or different weeks.

For example, the user accesses the user interface 600 on a first date, March 14. On this day, the particular question 630 is presented with a first display format. At a later time or date, such as on a second date, March 17, the same user accesses the query selection system 10 again. This time, the query selection system 10 presents graphical user interface 700 (FIG. 7). As shown, the second date 720 is indicated and the particular question previously shown in user interface 600 with the first display format is presented in a second display format 710, such as with a grey background (and no spelling or grammatical errors).

On the same day (e.g., the second date), a second user also accesses the query selection system 10 to obtain a list of questions. The query selection system 10 determines that the second user is in the same group as the first user, such as because they are both parents of children in the same class or school. In response, the query selection system 10 presents a user interface 800 to the second user. As shown, the second date 820 is indicated in the user interface 800 presented to the second user. The query selection system 10 determines that the second user has not been presented the particular question 630 with the second display format within the past three days (e.g., within a threshold period of time). However, the query selection system 10 determines that the particular question 630 was presented to the first user who is in the same group as the second user with the second display format. Accordingly, the query selection system 10 selects a third display format that was not used to present the particular question 630 to the first user or the second user for presenting the particular question 630 to the second user in the user interface 800. As shown in region 810, the third display format presents the particular question with a shaded background and with various spelling and grammatical errors intentionally introduced. The third display format shown in region 810 makes the text of the particular question 630 appear to be cut off which draws the user's attention.

Figure 9:
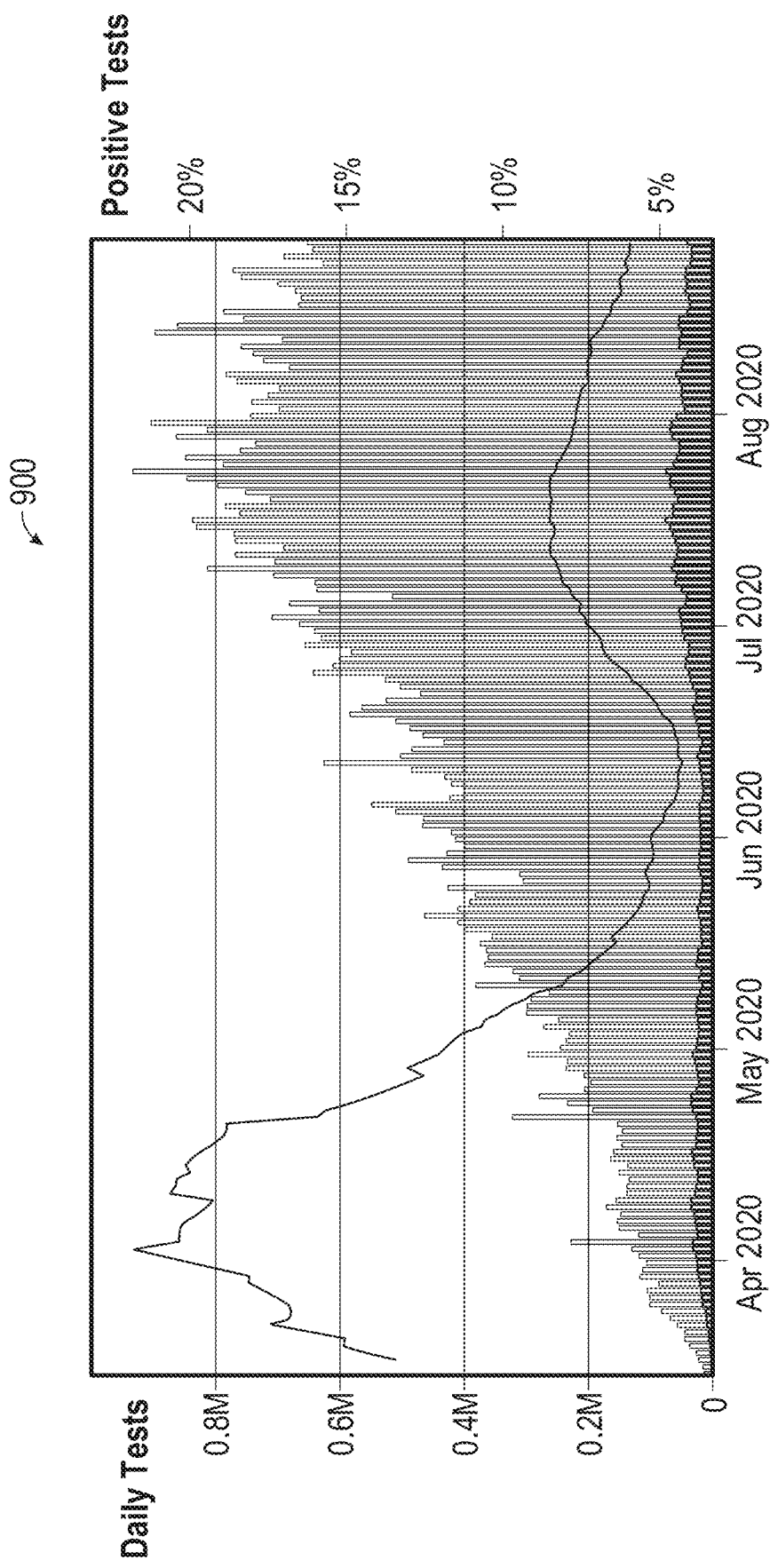
FIG. 9 is an example of a graphical user interface including infection rate information generated using information obtained from a database, according to some embodiments.

FIG. 9 is an example of a graphical user interface including infection rate information 900 that is generated using information obtained from a database, according to example embodiments. For example, the infection rate server 17 may maintain the infection rates for each region or a collection of regions. The infection rate server 17 may generate the infection rate information 900 based on the maintained infection rates. The infection rate server 17 accesses the maintained infection rate information 900 based on a particular region and particular time frame provided by the query selection system 10 to provide the current infection rate for the specified region.

The infection rate server 17 can also maintain information indicating how many or what percentage of individuals on a per region basis have been vaccinated. In some examples, the query selection system 10 can modify the list of questions that are selected for presentation to users based on the percentage of individuals in the region that have been vaccinated against the target infection. Namely, if a user is in a region with a vaccination rate that is lower than a threshold (e.g., lower than 80% vaccinated individuals), the query selection system 10 can present a first set of questions and/or in a first display format. If a second user is in a second region with a vaccination rate that is greater than the threshold (e.g., greater than 80% vaccinated individuals), the query selection system 10 can present a second set of questions and/or in a second display format.

Figure 10:
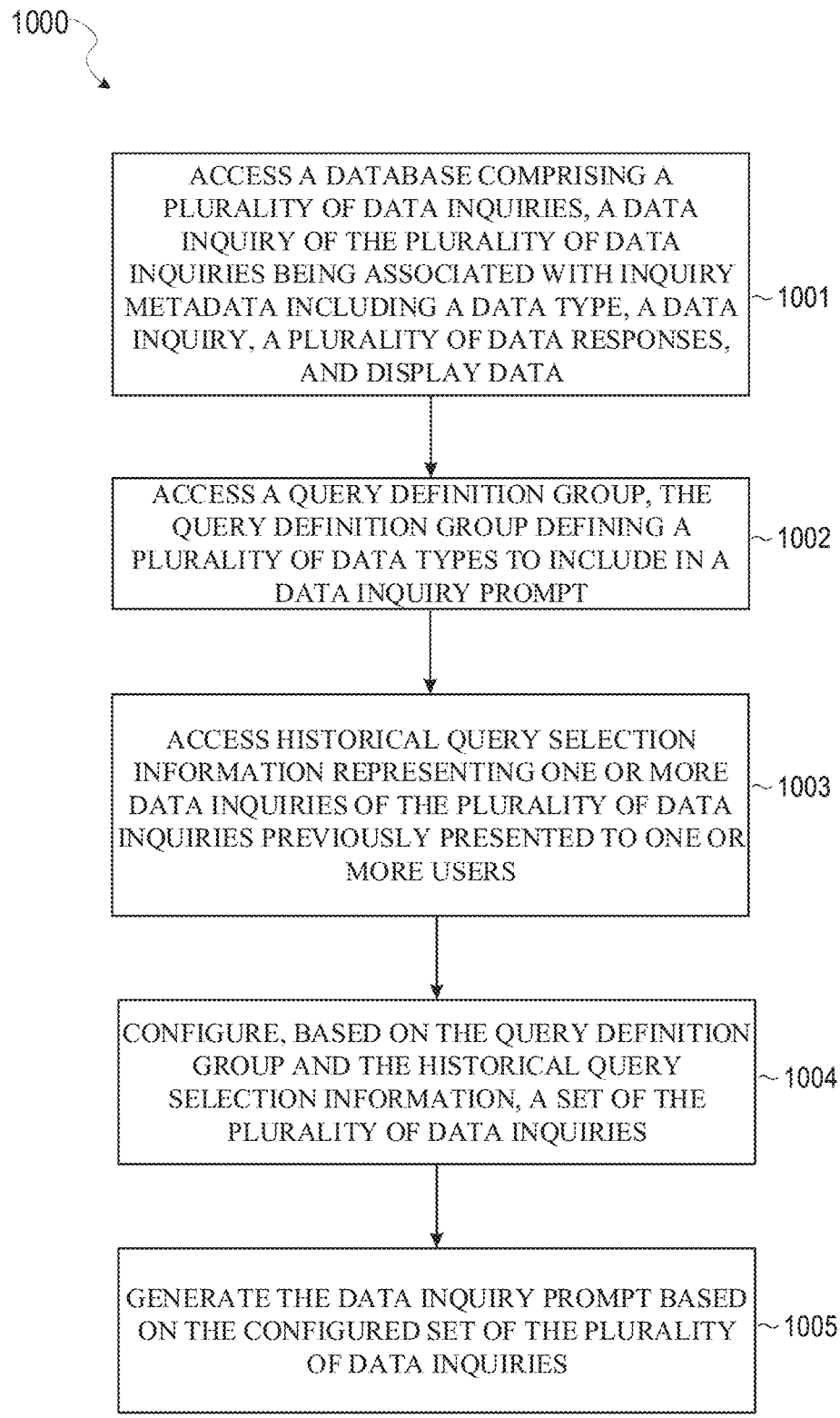
FIG. 10 is a flowchart illustrating example operations of the query selection system, according to some embodiments.

FIG. 10 is a flowchart illustrating example operations of the visually accessible website system in performing process 1000, according to example embodiments. The process 1000 may be embodied in computer-readable instructions for execution by one or more processors such that the operations of the process 1000 may be performed in part or in whole by the functional components of the system 1; accordingly, the process 1000 is described below by way of example with reference thereto. However, in other embodiments, at least some of the operations of the process 1000 may be deployed on various other hardware configurations. Some or all of the operations of process 1000 can be in parallel, out of order, or entirely omitted.

At operation 1001, the system 1 accesses a database comprising a plurality of data inquiries, a data inquiry of the plurality of data inquiries being associated with inquiry metadata including a data type, a data inquiry, a plurality of data responses, and display data.

At operation 1002, the system 1 accesses a query definition group, the query definition group defining a plurality of data types to include in a data inquiry prompt.

At operation 1003, the system 1 accesses historical query selection information representing one or more data inquiries of the plurality of data inquiries previously presented to one or more users (e.g., the one or more data inquiries were generated and caused to be displayed by a client device associated with the one or more users on a prior occasion).

At operation 1004, the system 1 configures, based on the query definition group and the historical query selection information, a set of the plurality of data inquiries.

At operation 1005, the system 1 generates the data inquiry prompt based on the configured set of the plurality of data inquiries and causes the data inquiry prompt to be displayed on a display device associated with the client device.

Figure 11:
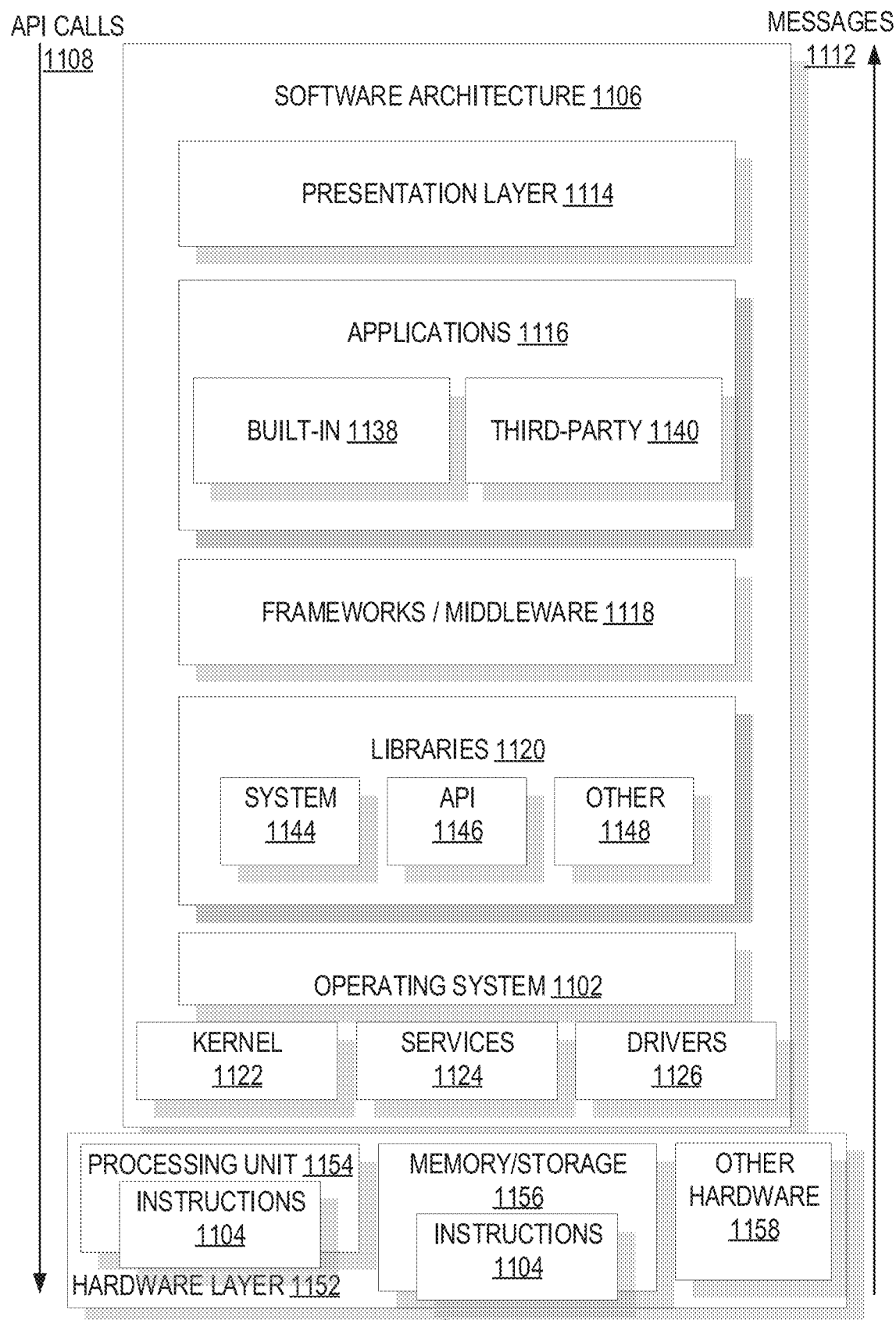
FIG. 11 is a block diagram illustrating an example software architecture, which may be used in conjunction with various hardware architectures herein described.

FIG. 11 is a block diagram illustrating an example software architecture 1106, which may be used in conjunction with various hardware architectures herein described. FIG. 11 is a non-limiting example of a software architecture and it will be appreciated that many other architectures may be implemented to facilitate the functionality described herein. The software architecture 1106 may execute on hardware such as machine 1200 of FIG. 12 that includes, among other things, processors 1204, memory 1214, and input/output (I/O) components 1218. A representative hardware layer 1152 is illustrated and can represent, for example, the machine 1200 of FIG. 12. The representative hardware layer 1152 includes a processing unit 1154 having associated executable instructions 1104. Executable instructions 1104 represent the executable instructions of the software architecture 1106, including implementation of the methods, components, and so forth described herein. The hardware layer 1152 also includes memory and/or storage devices memory/storage 1156, which also have executable instructions 1104. The hardware layer 1152 may also comprise other hardware 1158. The software architecture 1106 may be deployed in any one or more of the components shown in FIG. 1 or 2 (e.g., client device 11, system 2, infection rate server 17, or database 43). The software architecture 1106 can be utilized to generate a data inquiry prompt based on a set of data inquiries that are configured based on a query definition group and historical query selection information.

In the example architecture of FIG. 11, the software architecture 1106 may be conceptualized as a stack of layers where each layer provides particular functionality. For example, the software architecture 1106 may include layers such as an operating system 1102, libraries 1120, frameworks/middleware 1118, applications 1116, and a presentation layer 1114. Operationally, the applications 1116 and/or other components within the layers may invoke API calls 1108 through the software stack and receive messages 1112 in response to the API calls 1108. The layers illustrated are representative in nature and not all software architectures have all layers. For example, some mobile or special purpose operating systems may not provide a frameworks/middleware 1118, while others may provide such a layer. Other software architectures may include additional or different layers.

The operating system 1102 may manage hardware resources and provide common services. The operating system 1102 may include, for example, a kernel 1122, services 1124, and drivers 1126. The kernel 1122 may act as an abstraction layer between the hardware and the other software layers. For example, the kernel 1122 may be responsible for memory management, processor management (e.g., scheduling), component management, networking, security settings, and so on. The services 1124 may provide other common services for the other software layers. The drivers 1126 are responsible for controlling or interfacing with the underlying hardware. For instance, the drivers 1126 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 1120 provide a common infrastructure that is used by the applications 1116 and/or other components and/or layers. The libraries 1120 provide functionality that allows other software components to perform tasks in an easier fashion than to interface directly with the underlying operating system 1102 functionality (e.g., kernel 1122, services 1124 and/or drivers 1126). The libraries 1120 may include system libraries 1144 (e.g., C standard library) that may provide functions such as memory allocation functions, string manipulation functions, mathematical functions, and the like. In addition, the libraries 1120 may include API libraries 1146 such as media libraries (e.g., libraries to support presentation and manipulation of various media format such as MPREG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 1120 may also include a wide variety of other libraries 1148 to provide many other APIs to the applications 1116 and other software components/devices.

The frameworks/middleware 1118 (also sometimes referred to as middleware) provide a higher-level common infrastructure that may be used by the applications 1116 and/or other software components/devices. For example, the frameworks/middleware 1118 may provide various graphic user interface functions, high-level resource management, high-level location services, and so forth. The frameworks/middleware 1118 may provide a broad spectrum of other APIs that may be utilized by the applications 1116 and/or other software components/devices, some of which may be specific to a particular operating system 1102 or platform.

The applications 1116 include built-in applications 1138 and/or third-party applications 1140. Examples of representative built-in applications 1138 may include, but are not limited to, a contacts application, a browser application, a book reader application, a location application, a media application, a messaging application, and/or a game application. Third-party applications 1140 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 1140 may invoke the API calls 1108 provided by the mobile operating system (such as operating system 1102) to facilitate functionality described herein.

The applications 1116 may use built-in operating system functions (e.g., kernel 1122, services 1124, and/or drivers 1126), libraries 1120, and frameworks/middleware 1118 to create UIs to interact with users of the system. Alternatively, or additionally, in some systems, interactions with a user may occur through a presentation layer, such as presentation layer 1114. In these systems, the application/component "logic" can be separated from the aspects of the application/component that interact with a user.

Figure 12:
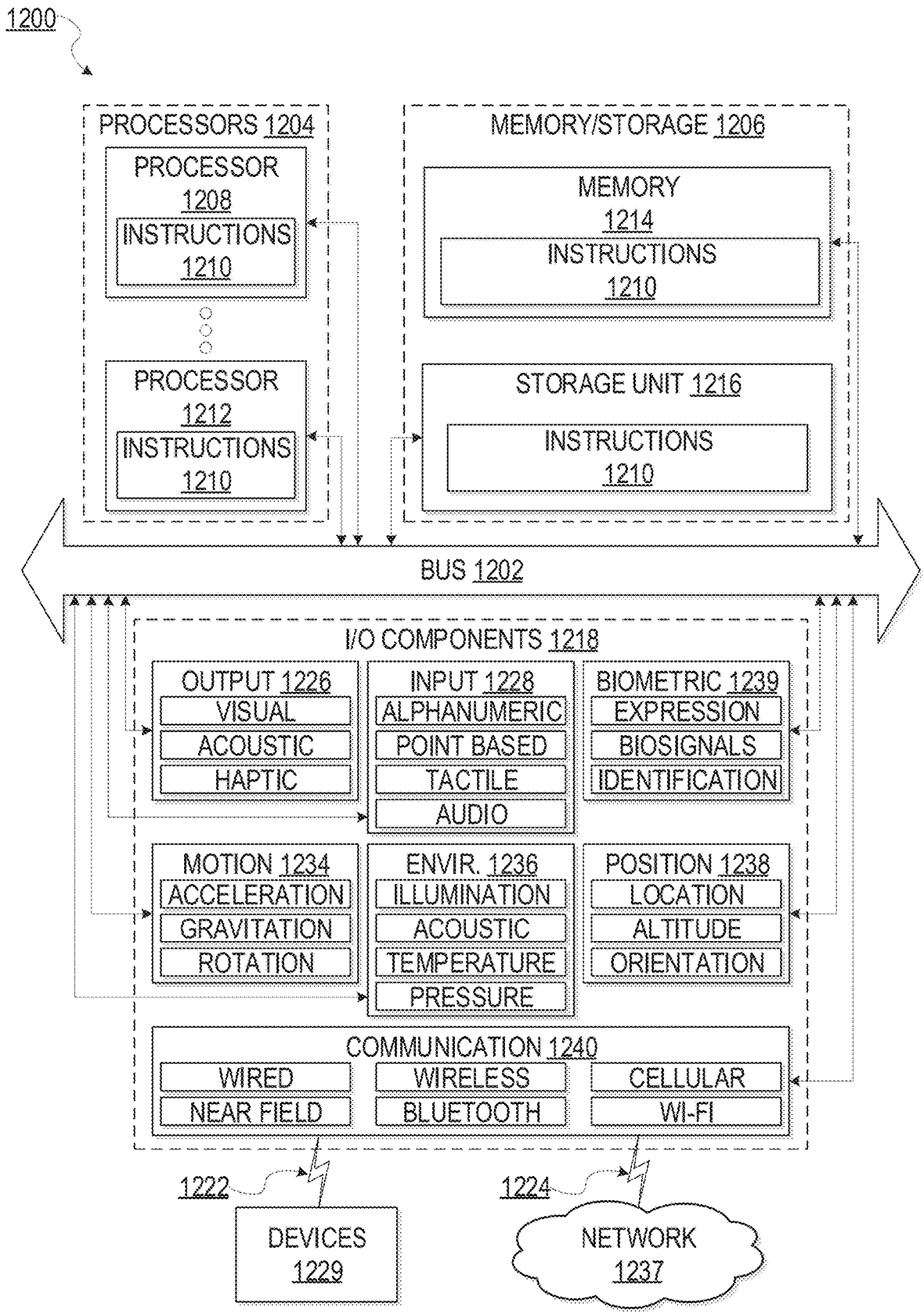
FIG. 12 is a block diagram illustrating components of a machine, according to some embodiments.

FIG. 12 is a block diagram illustrating components of a machine 1200, according to some example embodiments, able to read instructions from a machine-readable medium (e.g., a machine-readable storage medium) and perform any one or more of the methodologies discussed herein. Specifically, FIG. 12 shows a diagrammatic representation of the machine 1200 in the example form of a computer system, within which instructions 1210 (e.g., software, a program, an application, an applet, an app, or other executable code) for causing the machine 1200 to perform any one or more of the methodologies discussed herein may be executed. For example, the instructions 1210 may be executed by the query selection system 10 to generate a data inquiry prompt based on a set of data inquiries that are configured based on a query definition group and historical query selection information.

As such, the instructions 1210 may be used to implement devices or components described herein. The instructions 1210 transform the general, non-programmed machine 1200 into a particular machine 1200 programmed to carry out the described and illustrated functions in the manner described. In alternative embodiments, the machine 1200 operates as a standalone device or may be coupled (e.g., networked) to other machines. In a networked deployment, the machine 1200 may operate in the capacity of a server machine or a client machine in a server-client network environment, or as a peer machine in a peer-to-peer (or distributed) network environment. The machine 1200 may comprise, but not be limited to, electronic delivery detection 140, perishable item delivery server 105, smart home service provider server 107, device 132a, device 133a, device 134a, device 132b, device 133b, device 134b, a server computer, a client computer, a personal computer (PC), a tablet computer, a laptop computer, a netbook, a STB, a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1210, sequentially or otherwise, that specify actions to be taken by machine 1200. Further, while only a single machine 1200 is illustrated, the term "machine" shall also be taken to include a collection of machines that individually or jointly execute the instructions 1210 to perform any one or more of the methodologies discussed herein.

The machine 1200 may include processors 1204, memory/storage 1206, and I/O components 1218, which may be configured to communicate with each other such as via a bus 1202. In an example embodiment, the processors 1204 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 1208 and a processor 1212 that may execute the instructions 1210. The term "processor" is intended to include multi-core processors 1204 that may comprise two or more independent processors (sometimes referred to as "cores") that may execute instructions contemporaneously. Although FIG. 12 shows multiple processors 1204, the machine 1200 may include a single processor with a single core, a single processor with multiple cores (e.g., a multi-core processor), multiple processors with a single core, multiple processors with multiple cores, or any combination thereof.

The memory/storage 1206 may include a memory 1214, such as a main memory, or other memory storage, database 110, and a storage unit 1216, both accessible to the processors 1204 such as via the bus 1202. The storage unit 1216 and memory 1214 store the instructions 1210 embodying any one or more of the methodologies or functions described herein. The instructions 1210 may also reside, completely or partially, within the memory 1214, within the storage unit 1216, within at least one of the processors 1204 (e.g., within the processor's cache memory), or any suitable combination thereof, during execution thereof by the machine 1200. Accordingly, the memory 1214, the storage unit 1216, and the memory of processors 1204 are examples of machine-readable media.

The I/O components 1218 may include a wide variety of components to receive input, provide output, produce output, transmit information, exchange information, capture measurements, and so on, such as devices 132a-b, 133a-b, and 134a-b. The specific I/O components 1218 that are included in a particular machine 1200 will depend on the type of machine. For example, portable machines such as mobile phones will likely include a touch input device or other such input mechanisms, while a headless server machine will likely not include such a touch input device. It will be appreciated that the I/O components 1218 may include many other components that are not shown in FIG. 12. The I/O components 1218 are grouped according to functionality merely for simplifying the following discussion and the grouping is in no way limiting. In various example embodiments, the I/O components 1218 may include output components 1226 and input components 1228. The output components 1226 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1228 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 1218 may include biometric components 1239, motion components 1234, environmental components 1236, or position components 1238 among a wide array of other components. For example, the biometric components 1239 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1234 may include acceleration sensor components (e.g., accelerometer), gravitation sensor components, rotation sensor components (e.g., gyroscope), and so forth. The environmental components 1236 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1238 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1218 may include communication components 1240 operable to couple the machine 1200 to a network 1237 or devices 1229 via coupling 1224 and coupling 1222, respectively. For example, the communication components 1240 may include a network interface component or other suitable device to interface with the network 1237. In further examples, communication components 1240 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1229 may be another machine or any of a wide variety of peripheral devices (e.g., a peripheral device coupled via a USB).

Moreover, the communication components 1240 may detect identifiers or include components operable to detect identifiers. For example, the communication components 1240 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1240, such as location via Internet Protocol (IP) geo-location, location via Wi-Fi® signal triangulation, location via detecting a NFC beacon signal that may indicate a particular location, and so forth.

The present disclosure at times uses a two hour time window for purposes of illustration, e.g., 1-3 PM, 3-5 PM, etc. The present disclosure encompasses time windows of different lengths, e.g., one hour greater than two hours, four hours, or eight hours. The location-based model can adjust the length of a delivery time window based on the sensed data that a person is present at the location. These delivery time periods can be dynamic, e.g., a base window is two hours that can be started earlier or later depending on the likelihood that a person is present at the location.

Glossary

"CARRIER SIGNAL" in this context refers to any intangible medium that is capable of storing, encoding, or carrying transitory or non-transitory instructions for execution by the machine, and includes digital or analog communications signals or other intangible medium to facilitate communication of such instructions. Instructions may be transmitted or received over the network using a transitory or non-transitory transmission medium via a network interface device and using any one of a number of well-known transfer protocols.

"CLIENT DEVICE" in this context refers to any machine that interfaces to a communications network to obtain resources from one or more server systems or other client devices. A client device may be, but is not limited to, a mobile phone, desktop computer, laptop, PDA, smart phone, tablet, ultra book, netbook, laptop, multi-processor system, microprocessor-based or programmable consumer electronics, game console, set-top box, or any other communication device that a user may use to access a network.

"COMMUNICATIONS NETWORK" in this context refers to one or more portions of a network that may be an ad hoc network, an intranet, an extranet, a virtual private network (VPN), a LAN, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"MACHINE-READABLE MEDIUM" in this context refers to a component, device, or other tangible media able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"COMPONENT" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"PROCESSOR" in this context refers to any circuit or virtual circuit (a physical circuit emulated by logic executing on an actual processor) that manipulates data values according to control signals (e.g., "commands," "op codes," "machine code," etc.) and which produces corresponding output signals that are applied to operate a machine. A processor may, for example, be a CPU, a RISC processor, a CISC processor, a GPU, a DSP, an ASIC, a RFIC, or any combination thereof. A processor may further be a multi-core processor having two or more independent processors (sometimes referred to as "cores") that may execute instructions contemporaneously.

"TIMESTAMP" in this context refers to a sequence of characters or encoded information identifying when a certain event occurred, for example giving date and time of day, sometimes accurate to a small fraction of a second. The timestamps can be used on the electronic forms described herein to provide a date tracking of the form or the questions or the responses. In an example embodiment, the present disclosure may use the timestamps in the prior attestation forms, to change the pace of the queries presented on the interactive display. The device, by altering the timing of the display of queries, can increase the mindfulness of user interacting with attestation form by presenting questions with the same interval between query presentations or altering the time period between presenting the some of the queries. Accordingly, the user does not become conditioned to the timing of the attestation form being displayed on the screen.

The present system and methods can work to provide feedback on health status, e.g., infection rate, effect of change in medication delivery, effects of change in medication, effects of change in medication type, effects of change in medication packaging, and the like. The change in medication can be a change in prescription or a change in the formulation of the medication itself by the manufacturer. The change in medication packaging can be changing the medication from a bottle delivery to a blister package delivery. The present system can provide patient data with greater accuracy using the present systems and methods.

Changes and modifications may be made to the disclosed embodiments without departing from the scope of the present disclosure. These and other changes or modifications are intended to be included within the scope of the present disclosure, as expressed in the following claims.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
   accessing, by a server, a database comprising a plurality of data inquiries, a data inquiry of the plurality of data inquiries being associated with inquiry metadata including a data type, a plurality of data responses, and display data;
   accessing, by the server, a query definition group, the query definition group defining a plurality of data types to include in a data inquiry prompt;
   retrieving, by the server from the database, historical query selection information representing one or more data inquiries of the plurality of data inquiries previously caused to be displayed by client devices associated with one or more users;
   obtaining, based on the historical query selection information, historical data associated with the one or more users indicating which of the plurality of data inquiries were previously presented to the one or more users and a presentation format of the plurality of data inquiries that were previously presented to the one or more users;
   configuring, based on the query definition group and in response to obtaining the historical data associated with the one or more users, a set of the plurality of data inquiries, the set of the plurality of data inquiries comprising a subset of the plurality of data inquiries;
   generating the data inquiry prompt based on the configured subset of the plurality of data inquiries; and
   causing the data inquiry prompt to be displayed on a client device of a given user.

2. The method of claim 1, wherein:
   a first data inquiry of the plurality of data inquiries is associated with a first data type comprising at least one of health related information, social related information, geographical information, infection rate information, or industry related information; and
   a second data inquiry of the plurality of data inquiries is associated with a second data type, different form the first data type, comprising at least one of the health related information, the social related information, the geographical information, the infection rate information, or the industry related information.

3. The method of claim 2, wherein the health related information represents symptoms of a disease or virus or vaccination state, wherein the social related information represents travel information, location information, and social interaction information, and wherein the industry related information includes schools, retail, and manufacturing, and wherein configuring the set of the plurality of data inquiries comprises:
   determining an industry associated with the given user;
   identifying, based on the query definition group, a first set of the plurality of data inquiries associated with the data type corresponding to the determined industry; and forming a second set of data inquiries by selecting from the first set of the plurality of data inquiries at least one data inquiry associated with health related information and at least one data inquiry associated with social related information.

4. The method of claim 1, further comprising:
receiving, from a client device, input requesting display of the data inquiry prompt;
identifying a user associated with the client device;
retrieving historical query selection information for the identified user;
determining, based on the historical query selection information, display data for the set of the plurality of data inquiries indicating presentation format of the set of the plurality of data inquiries previously presented to the user; and
configuring one or more data inquiries in the set of the plurality of data inquiries included in the data inquiry prompt to have a different presentation format than the presentation format of the set of the plurality of data inquiries previously presented to the user.

5. The method of claim 4, wherein the historical query selection information indicates that a first of the set of the plurality of data inquiries was previously presented to the user using at least one of a first type of text font or color, a first type of graphical property, or a first type of background, a first spelling or grammatical error, and wherein the one or more data inquiries is configured to have a different presentation format comprising at least one of a second type of text font or color, a second type of graphical property, a second spelling or grammatical error, or a second type of background.

6. The method of claim 4, wherein the historical query selection information indicates that a first of the set of the plurality of data inquiries was previously presented to the user in a first position relative to the set of the plurality of data inquiries, and wherein the one or more data inquiries is configured to be presented to the user in a second position relative to the set of the plurality of data inquiries.

7. The method of claim 4, further comprising:
determining that a threshold period of time has elapsed since the set of the plurality of data inquiries was previously presented to the user; and
configuring the one or more data inquiries in the set of the plurality of data inquiries included in the data inquiry prompt to have the different presentation format in response to determining that the threshold period of time has elapsed.

8. The method of claim 4, further comprising:
retrieving a group identifier associated with the user;
accessing historical query selection information for a plurality of users associated with the group identifier, the historical query selection information for the plurality of users comprising display data for the set of the plurality of data inquiries indicating presentation format of the set of the plurality of data inquiries previously presented to the plurality of users; and
configuring the one or more data inquiries in the set of the plurality of data inquiries included in the data inquiry prompt to have a different presentation format than the presentation format of the set of the plurality of data inquiries previously presented to the plurality of users.

9. The method of claim 8, wherein the group identifier represents at least one of a set of users in a classroom, parents of the set of users in the classroom, or people in an organization that work within a threshold distance of each other in a same building.

10. The method of claim 1, further comprising:
receiving, from a first client device, input requesting display of the data inquiry prompt;
identifying a first geographical region associated with the first client device; and
retrieving, as the set of the plurality of data inquiries, one or more data inquiries of the plurality of data inquiries associated with the data type corresponding to the geographical region.

11. The method of claim 10, wherein the data inquiry prompt comprises a first data inquiry prompt, further comprising:
receiving, from a second client device, input requesting display of second data inquiry prompt;
identifying a second geographical region associated with the second client device; and
retrieving, as second set of the plurality of data inquiries included in the another data inquiry prompt, one or more data inquiries of the plurality of data inquiries associated with the data type corresponding to the second geographical region, the second data inquiry prompt comprising at least one of a different quantity of data inquires than the first data inquiry prompt or a different presentation format than the first data inquiry prompt.

12. The method of claim 10, further comprising:
retrieving, from one or more databases, a first infection or vaccination rate associated with the geographical region;
comparing that the first infection or vaccination rate to a threshold infection or vaccination rate; and
identifying a first data inquiry to include among the one or more data inquiries based on comparing that the first infection or vaccination rate to the threshold infection or vaccination rate.

13. The method of claim 12, wherein the first infection or vaccination rate corresponds to a first time interval, further comprising:
including the first data inquiry in the one or more data inquiries of the data inquiry prompt in response to determining that the first infection or vaccination rate exceeds the threshold infection or vaccination rate.

14. The method of claim 13, further comprising:
retrieving, from one or more databases, a second infection or vaccination rate associated with the geographical region corresponding to a second time interval; and
excluding the first data inquiry from the one or more data inquiries of the data inquiry prompt in response to determining that the second infection or vaccination rate is less than the threshold infection or vaccination rate.

15. The method of claim 12, further comprising:
repeating the first data inquiry in the data inquiry prompt in response to determining that the infection or vaccination rate exceeds the threshold infection or vaccination rate.

16. The method of claim 1, wherein configuration the set of the plurality of data inquiries comprises randomizing a presentation format of a first of the plurality of data inquiries.

17. The method of claim 16, wherein the first of the plurality of data inquiries for which the presentation format is randomized is associated with the data type corresponding to a specified data type.

18. A system comprising:
one or more processors coupled to a memory comprising non-transitory computer instructions that when executed by the one or more processors perform operations comprising:
- accessing, by a server, a database comprising a plurality of data inquiries, a data inquiry of the plurality of data inquiries being associated with inquiry metadata including a data type, a plurality of data responses, and display data;
- accessing, by the server, a query definition group, the query definition group defining a plurality of data types to include in a data inquiry prompt;
- retrieving, by the server from the database, historical query selection information representing one or more data inquiries of the plurality of data inquiries previously caused to be displayed by client devices associated with one or more users;
- obtaining, based on the historical query selection information, historical data associated with the one or more users indicating which of the plurality of data inquiries were previously presented to the one or more users and a presentation format of the plurality of data inquiries that were previously presented to the one or more users;
- configuring, based on the query definition group and in response to obtaining the historical data associated with the one or more users, a set of the plurality of data inquiries, the set of the plurality of data inquiries comprising a subset of the plurality of data inquiries;
- generating the data inquiry prompt based on the configured subset of the plurality of data inquiries; and
- causing the data inquiry prompt to be displayed on a client device of a given user.

19. A non-transitory computer readable medium comprising non-transitory computer-readable instructions for performing operations comprising:
- accessing, by a server, a database comprising a plurality of data inquiries, a data inquiry of the plurality of data inquiries being associated with inquiry metadata including a data type, a plurality of data responses, and display data;
- accessing, by the server, a query definition group, the query definition group defining a plurality of data types to include in a data inquiry prompt;
- retrieving, by the server from the database, historical query selection information representing one or more data inquiries of the plurality of data inquiries previously caused to be displayed by client devices associated with one or more users;
- obtaining, based on the historical query selection information, historical data associated with the one or more users indicating which of the plurality of data inquiries were previously presented to the one or more users and a presentation format of the plurality of data inquiries that were previously presented to the one or more users;
- configuring, based on the query definition group and in response to obtaining the historical data associated with the one or more users, a set of the plurality of data inquiries, the set of the plurality of data inquiries comprising a subset of the plurality of data inquiries;
- generating the data inquiry prompt based on the configured subset of the plurality of data inquiries; and
- causing the data inquiry prompt to be displayed on a client device of a given user.

20. A method comprising:
selecting, by at least one processor, a set of data inquiries from a plurality of data inquiries stored in a database based on a query definition group and a historical query selection information,
- each of the plurality of data inquiries being associated with inquiry metadata, the inquiry metadata comprising a data type, a data inquiry, a plurality of data responses, and display data,
- the query definition group defining a plurality of data types to include in a data inquiry prompt, and
- the historical query selection information representing one or more data inquiries being associated with responses previously received from client devices associated with one or more users;

generating the data inquiry prompt based on the set of data inquiries; and
causing the data inquiry prompt to be displayed by a client device associated with a given user.

21. The method of claim 20, further comprising:
obtaining, based on the historical query selection information, historical data associated with the one or more users indicating which of the one or more data inquiries were previously presented to the one or more users and a presentation format of the one or more data inquiries that were previously presented to the one or more users, the data inquiry prompt being generated in response to obtaining the historical data associated with the one or more users.

* * * * *